United States Patent
Kinomura et al.

(10) Patent No.: US 8,027,796 B2
(45) Date of Patent: Sep. 27, 2011

(54) S/N RATIO MEASURING METHOD IN EDDY CURRENT TESTING ON INTERNAL SURFACE OF PIPE OR TUBE

(75) Inventors: Shoji Kinomura, Takarazuka (JP); Yoshiyuki Nakao, Kobe (JP); Toshiya Kodai, Amagasaki (JP); Shugo Nishiyama, Takarazuka (JP)

(73) Assignee: Sumitomo Metal Industries, Ltd., Osaka (JP)

( * ) Notice: Subject to any disclaimer, the term of this patent is extended or adjusted under 35 U.S.C. 154(b) by 761 days.

(21) Appl. No.: 12/084,380

(22) PCT Filed: Oct. 27, 2006

(86) PCT No.: PCT/JP2006/321483
§ 371 (c)(1),
(2), (4) Date: Apr. 30, 2008

(87) PCT Pub. No.: WO2007/052550
PCT Pub. Date: May 10, 2007

(65) Prior Publication Data
US 2009/0138222 A1    May 28, 2009

(30) Foreign Application Priority Data
Oct. 31, 2005    (JP) .................. 2005-316319

(51) Int. Cl.
*G01R 29/26* (2006.01)
(52) U.S. Cl. ......................................... 702/69
(58) Field of Classification Search .................. 702/57, 702/59, 64, 65, 69–72, 77, 90, 108, 116, 702/147, 182, 183, 185, 189, 191, 193, 195; 324/76.83, 220, 238
See application file for complete search history.

(56) References Cited

U.S. PATENT DOCUMENTS

| | | | | |
|---|---|---|---|---|
| 4,303,885 A | * | 12/1981 | Davis et al. | 324/237 |
| 4,763,274 A | * | 8/1988 | Junker et al. | 702/38 |
| 5,623,204 A | * | 4/1997 | Wilkerson | 324/228 |
| 2004/0232911 A1 | * | 11/2004 | Schlicker et al. | 324/242 |

FOREIGN PATENT DOCUMENTS

| | | |
|---|---|---|
| JP | 61-34101 | 8/1986 |
| JP | 60-64247 | 4/1988 |
| JP | 1-223340 | 9/1989 |
| JP | 4-23971 | 4/1992 |

(Continued)

*Primary Examiner* — Mohamed Charioui
(74) *Attorney, Agent, or Firm* — Clark & Brody

(57) ABSTRACT

A method in accordance with the present invention includes the steps of: separating an eddy current signal into an X-axis component and a Y-axis component to obtain signal waveform data of the respective components; excluding predetermined low-frequency components respectively from the respective signal waveform data thus obtained; calculating a noise voltage value V1 defined by the following Equation (1) based upon voltage values X(i) and Y(i) of the signal waveform data of the X-axis component and the Y-axis component from which the low-frequency components have been excluded; and calculating an S/N ratio by dividing a voltage value D of an eddy current signal corresponding to a predetermined artificial flaw by the noise voltage value V1:

$$V1 = \pi/n \cdot \sum_{i=1}^{n} (X(i)^2 + Y(i)^2)^{1/2} \quad (1)$$

where n represents the number of samplings of the signal waveform data.

6 Claims, 3 Drawing Sheets

FOREIGN PATENT DOCUMENTS

| | | |
|---|---|---|
| JP | 4-41303 | 7/1992 |
| JP | 5-28962 | 4/1993 |
| JP | 8-211026 | 8/1996 |
| JP | 2595251 | 1/1997 |

\* cited by examiner

S/N RATIO MEASURING METHOD IN EDDY CURRENT TESTING ON INTERNAL SURFACE OF PIPE OR TUBE

TECHNICAL FIELD

The present invention relates to a method for measuring an S/N ratio (ratio of flaw signal to noise) in an eddy current testing on an internal surface of a pipe or tube that is carried out, for example, upon producing a pipe or tube for use as a heat exchanger pipe or tube arranged in a steam generator of a nuclear reactor, which provides effective measurements on the S/N ratio with high reliability. Hereinafter "pipe or tube" is generally referred to as "tube" when deemed appropriate.

BACKGROUND ART

Conventionally, a regular inspecting process for heat exchanger tubes arranged in a steam generator of a PWR-type nuclear reactor is carried out by using an eddy current testing on an internal surface of a tube. More specifically, the process is carried out as follows: When a flaw detecting coil is inserted onto an internal surface of a tube, with an AC voltage applied thereto, an AC magnetic field is generated so that an eddy current is induced on the tube internal surface. Since this eddy current differs depending on a material for a tube, the kind, dimension and the like of a defect, it is possible to carry out a non-destructive testing on the tube by measuring a generated state of the eddy current. Actually, the measurements on the eddy current are carried out by measuring a change in an electric current flowing through the flaw detecting coil, and by analyzing the measured signal (eddy current signal), the state of the tube internal surface can be evaluated. In general, the analysis on the eddy current signal is carried out by separating the eddy current signal into an X-axis component and a Y-axis component that are different from each other by 90° in their phases, and based upon a voltage value (peak-to-peak voltage value) of an eddy current signal indicated by the root of the sum of squares of the voltage values (peak-to-peak voltage values) of the respective components and the phase of the eddy current signal indicated by $\tan^{-1}$ (voltage value in the Y-axis component/voltage value in the X-axis component), the determination on a defect and noise and the identification on the kind of the defect and the like are executed.

In the above-mentioned eddy current testing, an eddy current signal (flaw signal) derived from a fine defect on the internal surface of a tube tends to be mingled with electrical noise inherent to the flaw detecting coil and the flaw detecting unit and noise caused by the degree of circularity of the tube internal surface and local fine irregularities thereon (these noises are generally referred to as "base noise". Namely, it is difficult to distinguish not only the voltage value, but also the frequency, from that of a defect, with the result that a defect that should originally be detected might be ignored. Therefore, so as not to ignore the defect that should be detected, there have been demands for reducing the voltage value of the base noise in the manufacturing steps of a tube. The manufacturer of tubes carries out an eddy current testing on the tube internal surface for each of tubes that have been manufactured, and informs the customer of a ratio of a voltage value of a flaw signal obtained by a predetermined artificial flaw to the voltage value of the base noise as an S/N ratio. Here, with respect to the factors that increase the base noise caused in association with the tube, factors such as irregularities in the outer diameter, the inner diameter and the thickness of a tube that has been subjected to a cold rolling process and a cold drawing process, a dimensional change due to the straightener, and a change in the thickness due to a polishing process on the tube surface; therefore, by taking these noise-increasing factors into consideration, the manufacturer produces tubes in a manner so as to satisfy the required specifications of the customer.

Specifically, the conventional measurements on the S/N ratio are carried out in the following manner. First, the measurement on the voltage value of the base noise has been carried out by allowing the operator to confirm a voltage value of an eddy current signal (eddy current signal waveform) obtained by carrying out an eddy current testing on the internal surface of a tube in an axis direction, through manual operations. More specifically, the operator visually reads the voltage value of an eddy current signal waveform outputted from a flaw detecting unit over the entire length of the tube, and the maximum value thereof is defined as a voltage value of the base noise. Alternatively, the operator visually reads the respective voltage values of signal waveforms in the X-axis component and Y-axis component outputted from a flaw detecting unit over the entire length of the tube, and the root of the sum of squares of the maximum voltage values of the respective components is defined as the voltage value of the base noise. Then, a voltage value of an eddy current signal or the root of the sum of squares of the respective voltage values in the X-axis component and Y-axis component, obtained by a predetermined artificial flaw is defined as the voltage value of a flaw signal, and the ratio of the voltage value of this flaw signal to the voltage value of the base noise is calculated as the S/N ratio.

However, in the above-mentioned conventional S/N ratio measuring method, the operator has to confirm waveforms of eddy current signals (or the X-axis component and Y-axis component thereof) over the entire length of a long tube, outputted from a flaw detecting unit, and by visually reading the maximum amplitude of each of these signal waveforms, the operator needs to determine the voltage value of the base noise. For this reason, a problem arises in which the working efficiency deteriorates (for example, it takes about one minute to measure the S/N ratio of one tube of about 20 m in length). Moreover, in some cases, it is difficult to determine whether the measured base noise is noise derived from the shape or the like of the tube, or electrical noise inherent to the flaw detecting unit or the like, and in such a case, an eddy current testing needs to be again carried out for confirmation so as to distinguish the cause of the noise generation. For this reason, more time is required, and another problem arises in which the higher degree of skill of the operator relating to the determination is required.

Here, in order to reduce the base noise, for example, Patent Document 1 (Japanese Patent Application Laid-Open No. 8-211026) has proposed an eddy current sensor probe that is designed so that prior to giving a detection signal detected by a flaw detecting coil to a signal cable, it is amplified by an amplifier. Moreover, Patent Document 2 (Japanese Utility Model Application Laid-Open No. 5-28962) has proposed a detecting probe for a fine tube in which, by attaching a probe head formed by a cylinder member made of synthetic resin to the front end of a flaw detecting probe so as to prevent rattling, noise generation due to a change in the inner diameter such as a tube expanding process or a tube constricting process can be prevented.

DISCLOSURE OF THE INVENTION

Even if the reduction of the base noise itself can be achieved by the related art disclosed in Patent Documents 1 and 2, the measuring process of the S/N ratio, in particular, the measuring process of the voltage value of base noise still has to be carried out by the operator through manual confirming operations of the voltage value of the eddy current signal waveform. Therefore, even when only the prior art disclosed in Patent Document 1 or 2 is used, the above-mentioned problem that the working efficiency on the S/N measurements is extremely poor and measuring results are greatly influenced by the skill, experience, conditions and the like of the operator to fail to provide reliable measurements can not be solved.

The present invention has been devised so as to solve the above-mentioned conventional problems, and its objective is to provide a method for measuring an S/N ratio that can measure the S/N ratio efficiently and provide an S/N ratio with high reliability in an eddy current testing on an internal surface of a pipe or tube.

In order to solve the above-mentioned problems, the present invention as described in claim 1 provides a method for measuring the S/N ratio in an eddy current testing on an internal surface of a pipe or tube, which is characterized by including the following steps A1 to D1.

(A1) First, by separating an eddy current signal obtained by executing an eddy current testing on an internal surface of a pipe or tube in an axis direction into an X-axis component and a Y-axis component that are different from each other by 90° in their phases, signal waveform data of the X-axis component and signal waveform data of the Y-axis component are obtained. In other words, in this step, for example, by inserting a flaw detecting probe having a flaw detecting coil into an internal surface of a pipe or tube so as to allow it to move in a pipe or tube axis direction, an eddy current signal waveform to be outputted from the flaw detecting probe is prepared, and in a flaw detecting unit, the signal waveform is separated into signal waveforms of an X-axis component and a Y-axis component that are different from each other by 90° in the phases thereof, and these are respectively A/D converted so that signal waveform data (signal waveform data of the X-axis component, signal waveform data of the Y-axis component) are generated as digital waveform data.

(B1) Next, predetermined low-frequency components are respectively excluded from the signal waveform data of the X-axis component and the signal waveform data of the Y-axis component thus obtained. Here, the cut-off frequency used for excluding the low-frequency component may be appropriately set so as to exclude signal components of frequencies corresponding to moderate fluctuations in the voltage value caused by moderate fluctuations in the inner diameter and the thickness of a pipe or tube along the axis direction of the pipe or tube, as well as by the rocking (liftoff: positional deviations between the pipe or tube axis and the center of the flaw detecting probe) due to shifts of the flaw detecting probe, without excluding signal components of frequencies corresponding to defects such as flaws and damages. Thus, the voltage value of base noise, which is difficult to distinguish from defects with respect to the frequency, can be appropriately evaluated. Here, with respect to the method for excluding the low-frequency component, not particularly limited, various conventionally known filtering methods may be used.

(C1) Next, based upon a voltage value X(i) of the signal waveform data of the X-axis component with the low-frequency component excluded therefrom and a voltage value Y(i) of the signal waveform data of the Y-axis component with the low-frequency component excluded therefrom, a noise voltage value V1 defined by the following Equation (1) is calculated.

[Equation 1]

$$V1 = \pi/n \cdot \sum_{i=1}^{n}(X(i)^2 + Y(i)^2)^{1/2} \quad (1)$$

where n represents the number of samplings of the signal waveform data.

Here, what is meant by the noise voltage value V1 defined by the above-mentioned Equation (1) is virtually explained as follows: That is, the root ($=(X(i)^2+Y(i)^2)^{1/2}$) of the sum of squares of the voltage value X(i) and the voltage value Y(i) of the respective signal waveform data at each of sampling points (i=1 to n) is calculated, and after the calculated values have been added with respect to all the sampling points, the resulting value is divided by the sampling number n. The calculated value obtained by the above-mentioned calculations corresponds to an average value of the full-wave rectified wave, in the case when the eddy current signal waveform is full-wave rectified. Here, it has been known that, supposing that a signal waveform is a sine wave, in an attempt to calculate the amplitude (one-side amplitude) of the signal waveform from the average value of the full-wave rectified wave thereof, it is only necessary to multiply the average value by $\pi/2$. Therefore, in the present step, supposing that the eddy current signal waveform is a sine wave, the above-mentioned calculated value (corresponding to the average value of the full-wave rectified wave) is multiplied by $\pi/2$. The calculated value obtained by these calculations corresponds to the one-side amplitude on the assumption that the eddy current signal waveform is a sine wave. Lastly, by multiplying the calculated value by 2, the noise voltage value V1 is calculated. The noise voltage value V1, obtained through the above-mentioned calculations (that is, defined by Equation (1)), corresponds to a peak-to-peak voltage value on the assumption that the eddy current signal waveform is a sine wave.

(D1) Lastly, based upon a voltage value (peak-to-peak voltage value) D of an eddy current signal corresponding to a predetermined artificial flaw, obtained by executing an eddy current testing on an internal surface of a pipe or tube with the artificial flaw formed therein, and the noise voltage value V1, an S/N ratio defined by the following Equation (2) is calculated. Here, upon calculating the S/N ratio, for example, an artificial flaw is formed in one pipe or tube made from a predetermined material with a predetermined dimension, and by adjusting the sensitivity of a flaw detecting unit so as to output a predetermined voltage value with respect to the one pipe or tube as the voltage value D, only the measurement on the noise voltage value V1 may be carried out on each of tubes by utilizing the resulting sensitivity.

[Equation 2]

$$S/N \text{ ratio} = D/V1 \quad (2)$$

As described above, in the method for measuring an S/N ratio of the present invention, signal waveform data of the X-axis component and Y-axis component of an eddy current signal that has been obtained by carrying out an eddy current testing on an internal surface of a pipe or tube in the axis direction are obtained, and after predetermined low-frequency components have been excluded therefrom, an S/N ratio is calculated based upon the above-mentioned Equations (1) and (2). Therefore, by utilizing, for example, a computer in which a program for excluding the low-frequency components and programs for executing calculations based upon Equations (1) and (2) are installed, at least a sequence of operations after obtaining the signal waveform data can be automatically executed, and the S/N ratio can be consequently obtained with high efficiency. Moreover, since the S/N ratio is calculated constantly in accordance with Equations (1) and (2), it becomes possible to obtain measuring results with high reliability without being influenced by the skill, experience, conditions and the like of the operator, which makes the present method different from the conventional one.

In the invention relating to claim 1, as shown in Equation (1), the root of the sum of squares of the voltage value X(i) and the voltage value Y(i) at each of sampling points is calculated, and after the calculated values have been added with respect to all the sampling points (i=1 to n), the resulting value is divided by the sampling number n. In other words, the voltage values of eddy current signals at all the sampling points are averaged, and by using the averaged value, the noise voltage value V1 is calculated; therefore, in a state where there are great irregularities in the distribution of noise in the axis direction of the pipe or tube, there is the possibility that the noise voltage value V1 to be calculated might be estimated as a level lower than that of the actual noise voltage level.

In order to reduce the possibility of such a low level estimation, signal waveform data of the X-axis component and signal waveform data of the Y-axis component are divided into a plurality of sections in the axis direction of the pipe or tube, and the voltage values of eddy current signals are averaged for each of the divided sections so that the noise voltage value is calculated for each section, and the maximum value over the entire sections of these calculated noise voltage values may be defined as a noise voltage value to be used for the S/N ratio measurements.

That is, in order to solve the above-mentioned problems, the present invention as described in claim 2 provides a method for measuring the S/N ratio in an eddy current testing on an internal surface of a pipe or tube, which is characterized by including the following steps A2 to E2.

(A2) First, by separating an eddy current signal obtained by executing an eddy current testing on an internal surface of a pipe or tube in an axis direction into an X-axis component and a Y-axis component that are different from each other by 90° in their phases, signal waveform data of the X-axis component and signal waveform data of the Y-axis component are obtained.

(B2) Next, predetermined low-frequency components are respectively excluded from the signal waveform data of the X-axis component and the signal waveform data of the Y-axis component thus obtained.

(C2) Next, the signal waveform data of the X-axis component with the low-frequency component excluded therefrom and the signal waveform data of the Y-axis component with the low-frequency component excluded therefrom are respectively divided into signal waveform data for each of a plurality of sections j (j=1 to N, N: an integer of 2 or more) in the axis direction of the pipe or tube.

(D2) Next, based upon a voltage value X(i, j) of the signal waveform data of the X-axis component with the low-frequency component excluded therefrom and a voltage value Y(i, j) of the signal waveform data of the Y-axis component with the low-frequency component excluded therefrom, a noise voltage value V2(j) defined by the following Equation (3) is calculated for each of the divided sections j.

[Equation 3]

$$V2(j) = \pi/m \cdot \sum_{i=1}^{m}(X(i, j)^2 + Y(i, j)^2)^{1/2} \quad (3)$$

where m represents the number of samplings of the signal waveform data in each section, (E2) Lastly, based upon a voltage value (peak-to-peak voltage value) D of an eddy current signal corresponding to a predetermined artificial flaw, obtained by executing an eddy current testing on an internal surface of a pipe or tube with the artificial flaw formed therein, as well as based upon a maximum value V2 over the entire sections of the noise voltage value V2(j)) calculated for each of the sections j, an S/N ratio defined by the following Equation (4) is calculated.

[Equation 4]

$$S/N \text{ ratio} = D/V2 \quad (4)$$

As described above, in the invention relating to claim 2, after a predetermined low-frequency component has been excluded in step B2 from the signal waveform data of the X-axis component and the signal waveform data of the Y-axis component obtained in step A2, the resulting signal waveform data are divided into signal waveform data for each of a plurality of sections in the axis direction of the pipe or tube in step C2. However, the present invention is not intended to be limited by this arrangement, and the orders of the step B2 and step C2 may be exchanged so that, after the obtained signal waveform data of the X-axis component and signal waveform data of the Y-axis component have been divided into signal waveform data for each of a plurality of sections in the axis direction of the pipe or tube, a predetermined low-frequency component may be excluded for each of the sections.

That is, in order to solve the above-mentioned problems, the present invention as described in claim 3 provides a method for measuring the S/N ratio in an eddy current testing on an internal surface of a pipe or tube, which is characterized by including the following steps A3 to E3.

(A3) First, by separating an eddy current signal obtained by executing an eddy current testing on an internal surface of a pipe or tube in an axis direction into an X-axis component and a Y-axis component that are different from each other by 90° in their phases, signal waveform data of the X-axis component and signal waveform data of the Y-axis component are obtained.

(B3) Next, the signal waveform data of the X-axis component and the signal waveform data of the Y-axis component thus obtained are respectively divided into signal waveform data for each of a plurality of sections j (j=1 to N, N: an integer of 2 or more) in the axis direction of the pipe or tube.

(C3) Next, predetermined low-frequency components are respectively excluded from the signal waveform data of the X-axis component and the signal waveform data of the Y-axis component for each of the divided sections j.

(D3) Next, based upon a voltage value X(i, j) of the signal waveform data of the X-axis component with the low-frequency component excluded therefrom and a voltage value Y(i, j) of the signal waveform data of the Y-axis component with the low-frequency component excluded therefrom, a noise voltage value V2(j) defined by the following Equation (3) is calculated for each of the divided sections j.

[Equation 5]

$$V2(j) = \pi/m \cdot \sum_{i=1}^{m}(X(i, j)^2 + Y(i, j)^2)^{1/2} \quad (3)$$

where m represents the number of samplings of the signal waveform data in each section.

(E3) Lastly, based upon a voltage value (peak-to-peak voltage value) D of an eddy current signal corresponding to a predetermined artificial flaw, obtained by executing an eddy current testing on an internal surface of a pipe or tube with the artificial flaw formed therein, as well as based upon a maximum value V2 over the entire sections of the noise voltage value V2(j) calculated for each of the sections j, an S/N ratio defined by the following Equation (4) is calculated.

[Equation 6]

$$S/N \text{ ratio} = D/V2 \tag{4}$$

Here, in the inventions relating to the above-mentioned claims 1 to 3, although the method for excluding a predetermined low-frequency component is not particularly limited as described above in the invention of claim 1, a filtering method using a Fourier transform is preferably used from the viewpoint of a high-speed process with high filtering precision.

That is, as described in claim 4, the step of excluding a predetermined low-frequency component in the inventions relating to claims 1 to 3 may preferably include the following steps a to c.

(a) By respectively applying a Fourier transform to the signal waveform data of the X-axis component and the signal waveform data of the Y-axis component, a frequency spectrum is extracted.

(b) Next, the low-frequency component is excluded from the extracted frequency spectrum.

(c) Lastly, by respectively applying an Inverse Fourier transform to the frequency spectrum from which the low-frequency component has been excluded, signal waveform data of the X-axis component with the low-frequency component excluded therefrom and signal waveform data of the Y-axis component with the low-frequency component excluded therefrom are generated.

In accordance with a method for measuring the S/N ratio in an eddy current testing on an internal surface of a pipe or tube relating to the present invention, the S/N ratio can be measured with high efficiency and the S/N ratio can be provided with high reliability.

BEST MODE FOR CARRYING OUT THE INVENTION

Referring to attached drawings on demand, the following description will discuss an S/N ratio measuring method for an eddy current testing to be carried out on an internal surface of a tube in accordance with one embodiment of the present invention.

Figure 1:
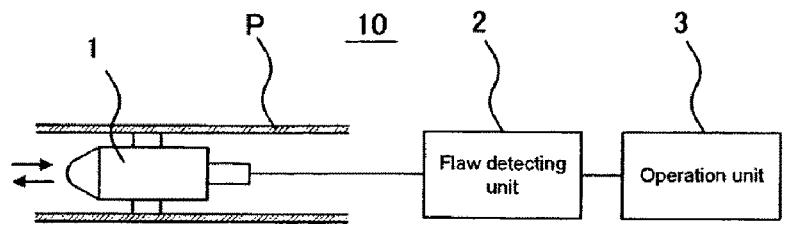
FIG. 1 is a diagram that schematically shows a structure of an eddy current testing unit used for carrying out an S/N ratio measuring method in accordance with one embodiment of the present invention.

FIG. 1 is a diagram that schematically shows a structure of an eddy current testing unit used for carrying out an S/N ratio measuring method in accordance with the present embodiment. As shown in FIG. 1, an eddy current testing unit 10 in accordance with the present embodiment is provided with a flaw detecting probe 1, a flaw detecting unit 2 and an operation unit 3.

The flaw detecting probe 1 has a flaw detecting coil (not shown) attached to a predetermined portion thereof, and is designed so that it is inserted onto an internal surface of a tube P with the center of the flaw detecting probe 1 and the axis of the tube P being virtually made coincident with each other, and moved along the axis direction of the tube P by a conventionally known propelling mechanism (not shown) virtually at a constant velocity. In this case, by applying an AC voltage to the flaw detecting coil of the flaw detecting probe 1, an AC magnetic field is generated so that an eddy current is induced on the internal surface of the tube P. Thus, a change in the electric current flowing through the flaw detecting coil, which takes place in response to the material of the tube P, a kind, a dimension or the like of a defect that is present in the tube P, is outputted to the flaw detecting unit 2 as an eddy current signal.

The flaw detecting unit 2 applies an AC voltage to the flaw detecting coil of the flaw detecting probe 1 as described above, and also separates the eddy current signal waveform outputted from the flaw detecting probe 1 into signal waveforms of an X-axis component and a Y-axis component that are different from each other by 90° in their phases. Moreover, the flaw detecting unit 2 A/D converts the respective signal waveforms to generate signal waveform data as digital data (signal waveform data of the X-axis component, and signal waveform data of the Y-axis component). The respective signal waveform data thus generated are outputted to the operation unit 3. Here, since the separation of the X-axis component and the Y-axis component is carried out by using a known means, such as a phase shifter and a phase detector (not shown) in the same manner as in a general-use flaw detecting unit, the detailed description thereof will be omitted from the present specification. Moreover, in the same manner as in a general-use flaw detecting unit, the flaw detecting unit 2 is designed to be capable of outputting an eddy current signal waveform prior to the separation into the X-axis component and the Y-axis component.

The operation unit 3 is formed by a general-use computer, such as a work station and a personal computer, provided with an input/output interface for various data between the operation unit 3 and the flaw detecting unit 2, an external storage device (optical disc, etc.) used for storing signal waveform data inputted from the flaw detecting unit 2 and the like, in addition to a CPU, a ROM and a RAM. Here, the operation unit 3 is provided with a program used and installed therein so as to execute operation processes, which will be described later, on the signal waveform data (stored in the external storage device) inputted from the flaw detecting unit 2. Upon completion of obtaining signal waveform data of the X-axis component and signal waveform data of the Y-axis component with respect to one or a plurality of tubes P (or storing the data into the external storage device), the operation unit 3 reads the respective stored signal waveform data from the external storage device, and executes operation processes thereon in accordance with the program. The following description will discuss in detail the contents of the operation processes in the operation unit 3, which form a feature of an S/N ratio measuring method in accordance with the present embodiment.

First, the operation unit 3 respectively excludes predetermined low-frequency components from the signal waveform data of the X-axis component and signal waveform data of the Y-axis component obtained as described above. A cut-off frequency corresponding to the low-frequency component to be excluded is appropriately set preliminarily based upon the results of an eddy current testing and the like so as not to exclude signal components of frequencies corresponding to defects such as flaws and damages, and also so as to exclude signal components of frequencies corresponding to moderate fluctuations in the voltage value caused by moderate fluctuations of the inner diameter of a tube P along the axis direction of the tube P and rocking or the like due to the shift of the flaw detecting probe 1, and stored therein. For example, supposing that a shifting velocity of the flaw detecting probe 1 is 305 mm/sec(=12.0 inches/sec), the cut-off frequency is preferably set in a range from 100 to 300 Hz.

With respect to the method for excluding a low-frequency component, although not particularly limited, the present embodiment adopts a filtering method using a Fourier transform from the viewpoint of a high-speed process with high filtering precision. More specifically, the operation unit 3 is designed to successively execute the following steps a to c.

(a) By applying a Fourier transform (Fast Fourier Transform Algorithm (FFT)) to each of the signal waveform data of the X-axis component and the signal waveform data of the Y-axis component, a frequency spectrum is extracted.

(b) Next, from the extracted frequency spectrum, a low-frequency component below the cut-off frequency that has been set as described above is extracted.

Figure 2:
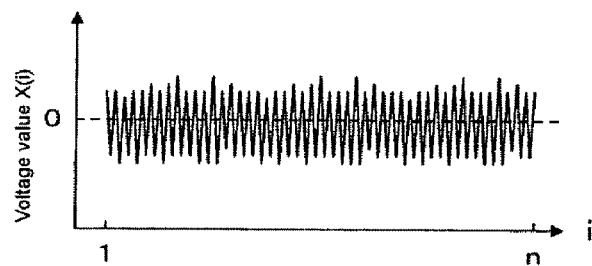
FIG. 2 is a graph that schematically shows signal waveform data of an X-axis component with the low-frequency component excluded therefrom, which is generated by the eddy current testing unit shown in FIG. 1 (an explanatory graph that explains an operation method for a noise voltage value V1 to be calculated by the eddy current testing unit shown in FIG. 1).

(c) Lastly, by applying an Inverse Fourier transform (Inverse Fast Fourier Transform Algorithm (IFFT) to the frequency spectrum from which the low-frequency component has been excluded, signal waveform data of the X-axis component with the low-frequency component excluded therefrom and signal waveform data of the Y-axis component with the low-frequency component excluded therefrom are generated. FIG. 2 is a graph that schematically shows the signal waveform data of the X-axis component generated as described above. Here, although not shown in the drawings, the signal waveform data of the Y-axis component generated as described above also form the same waveform as that shown in FIG. 2.

Next, based upon the voltage value X(i) of the signal waveform data of the X-axis component with the low-frequency component excluded therefrom and the voltage value Y(i) of the signal waveform data of the Y-axis component with the low-frequency component excluded therefrom, the operation unit 3 calculates a noise voltage value V1 defined by the following Equation (1).

[Equation 7]

$$V1 = \pi/n \cdot \sum_{i=1}^{n} (X(i)^2 + Y(i)^2)^{1/2} \qquad (1)$$

where n represents the number of samplings of the signal waveform data.

That is, the root of the sum of squares of the voltage value X(i) of the signal waveform data of the X-axis component and the voltage value Y(i) of the signal waveform data of the Y-axis component at each of sampling points i (i=1 to n) shown in FIG. 2 is calculated, and after the calculated values have been added with respect to all the sampling points, the value obtained by multiplying the resulting value by $\pi/n$ is defined as the noise voltage value V1. As has been described earlier, this noise voltage value V1 is a value corresponding to a peak-to-peak voltage value obtained on the assumption that the eddy current signal waveform is a sine wave.

Lastly, by executing an eddy current testing on the internal surface of a tube in which a predetermined artificial flaw has been formed, the voltage value (peak-to-peak voltage value) D of an eddy current signal corresponding to the artificial flaw is obtained, and based upon this value and the above-mentioned noise voltage value V1, the operation unit 3 calculates an S/N ratio defined by the following Equation (2). Here, in the present embodiment, the voltage value D corresponding to the artificial flaw obtained by executing an eddy current testing on a predetermined tube with the artificial flaw formed therein has been preliminarily stored in the operation unit 3, and upon carrying out an S/N ratio measurement on each of other tubes P (calculation of the S/N ratio defined by Equation (2)), only the measurement on the noise voltage value V1 is carried out on each tube P with the sensitivity of a flaw detecting unit 2 in which the eddy current signal corresponding to the artificial flaw has been set to a specific voltage value, while the preliminarily stored voltage value D is used as the voltage value D.

[Equation 8]

$$S/N \text{ ratio} = D/V1 \qquad (2)$$

As described above, in accordance with the S/N ratio measuring method carried out by the eddy current testing unit 10 relating to the present embodiment, since the sequence of measuring operations are automatically carried out, the S/N ratio can be measured with high efficiency. Moreover, since the S/N ratio can be calculated constantly in accordance with Equations (1) and (2), it becomes possible to obtain measured results with high reliability without being affected by the skill, experience, conditions and the like of the operator, which makes the present method different from the conventional one.

Here, the present embodiment has exemplified a method in which, as shown in Equation (1), the operation unit 3 calculates the root of the sum of squares of the voltage value X(i) and the voltage value Y(i) at each of sampling points, and after adding the calculated values with respect to all the sampling points, multiplies the resulting value by $\pi/n$ so that the value thus calculated is used as the noise voltage value V1. However, the present invention is not intended to be limited by this method, and another method may be used in which the operation unit 3 divides the signal waveform data of the X-axis component and the signal waveform data of the Y-axis component into a plurality of sections in the axis direction of the tube P, and after calculations have been carried out on each of the divided sections in the same manner as in the present embodiment, the maximum value in the entire sections of noise voltage values, each calculated for each of the sections, is defined as a noise voltage value to be used for the S/N ratio measurement.

Figure 3:
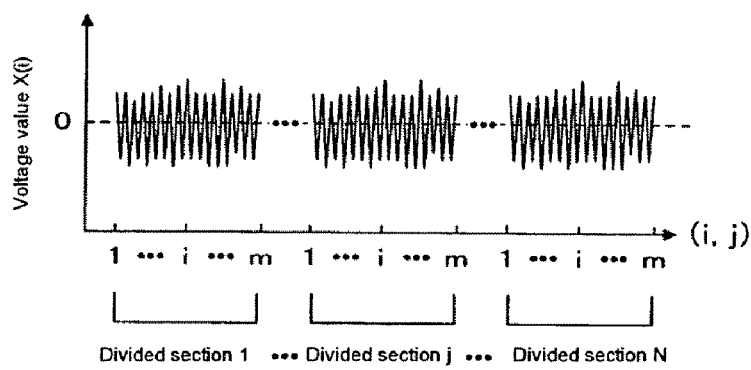
FIG. 3 is a graph that schematically shows signal waveform data of an X-axis component with the low-frequency component excluded therefrom, which is generated by the eddy current testing unit shown in FIG. 1 (an explanatory graph that explains an operation method for a noise voltage value V2 to be calculated by the eddy current testing unit shown in FIG. 1).

More specifically, as shown in FIG. 3, the operation unit 3 divides the signal waveform data of the X-axis component and the signal waveform data of the Y-axis component, with the low-frequency components respectively excluded therefrom in the same manner as in the above-mentioned embodiment, into signal waveform data for each of a plurality of sections j (j=1 to N, N: an integer of 2 or more) in the axis direction of the tube P. Next, based upon the voltage value X (i, j) of signal waveform data of the X-axis component and the voltage value Y (i, j) of signal waveform data of the Y-axis component, the operation unit 3 calculates a noise voltage value V2(j) defined by the following Equation (3) for each of the divided sections j.

[Equation 9]

$$V2(j) = \pi/m \cdot \sum_{i=1}^{m}(X(i, j)^2 + Y(i, j)^2)^{1/2} \quad (3)$$

where m represents the number of samplings of the signal waveform data in each section.

Lastly, based upon the voltage value D (peak-to-peak voltage value) of an eddy current signal corresponding to an artificial flaw obtained by executing an eddy current testing on the internal surface of a tube in which the artificial flaw has been formed and the maximum value V2 in the entire sections of noise voltage values V2(j), each calculated for each section j, the operation unit 3 calculates the S/N ratio defined by the following Equation (4):

[Equation 10]

$$S/N \text{ ratio} = D/V2 \quad (4)$$

Even in a state where there are great irregularities in the distribution of noise in the axis direction of the tube P, by using the above-mentioned method, it becomes possible to reduce the possibility that the noise voltage value to be used for the S/N measurement might be estimated as a level lower than that of the actual noise level.

Here, the above-mentioned operation processes to be executed by the operation unit 3 are designed so that, after predetermined low-frequency components have been excluded from obtained signal waveform data of the X-axis component and signal waveform data of the Y-axis component, the resulting data are divided into signal waveform data for each of a plurality of sections in the axis direction of the tube P. However, another method in which, after the obtained signal waveform data of the X-axis component and signal waveform data of the Y-axis component have been preliminarily divided into signal waveform data for each of a plurality of sections in the axis direction of the tube P, a predetermined low-frequency component is excluded therefrom for each of the sections may be used with the same functions and effects.

The features of the present invention will be further clarified by means of Examples and Comparative Examples shown below.

EXAMPLE 1

By using an eddy current testing unit having the same structure as that shown in FIG. 1, the S/N ratio defined by the above-mentioned Equation (2) was automatically measured under flaw detecting conditions shown in the following Table 1.

TABLE 1

| Sampling Rate | 500 points/sec |
| Flaw Detecting Probe Velocity | 305 mm/sec |
| Distance between Sampling Points | 0.61 mm |
| Length of Tube | 20000 mm |

Here, upon measuring the voltage value D of an eddy current signal corresponding to an artificial flaw, a tube having through holes, each having 0.66 mm in diameter, formed at four positions in a circumferential direction with pitches of 90° as artificial flaws, was used. Moreover, upon measuring the noise voltage value V1, a tube, made of the same material with the same dimension as those of the above-mentioned tube, with no artificial flaws formed therein, was used, and the eddy current testing was carried out over the entire length of the tube. With respect to the method for excluding a low-frequency component, a filtering method using a Fourier transform was used.

Figure 4:
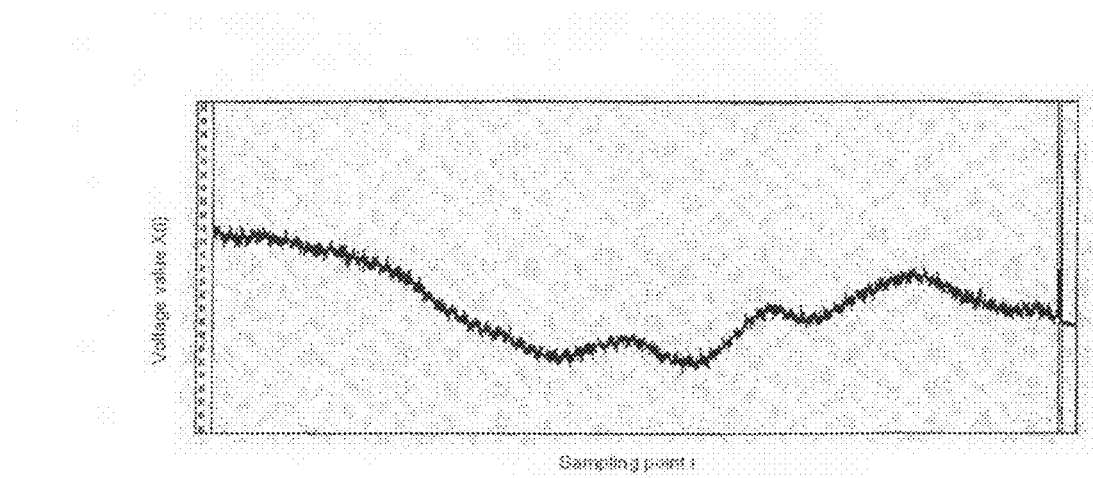
FIG. 4 shows signal waveform data of an X-axis component prior to excluding a low-frequency component relating to embodiment 1 of the present invention.
Figure 5:
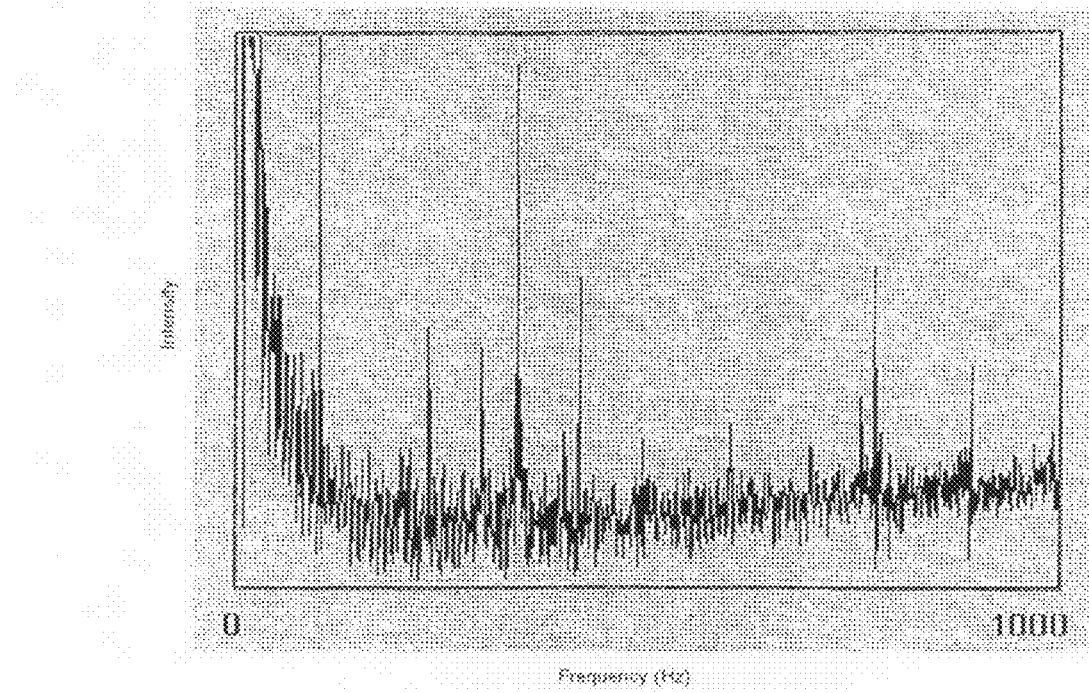
FIG. 5 shows a frequency spectrum extracted by applying a Fourier transform (FFT) to signal waveform data shown in FIG. 4.
Figure 6:
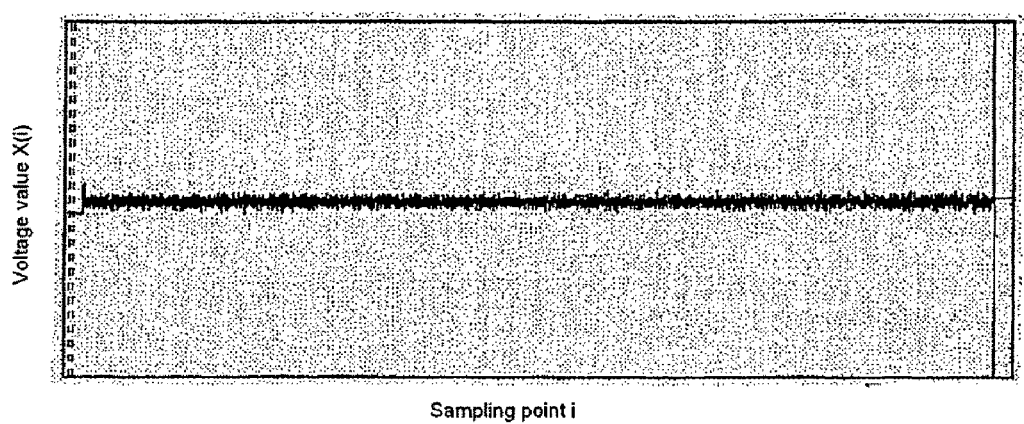
FIG. 6 shows signal waveform data of the X-axis component generated by applying an Inverse Fourier transform (IFFT) to the frequency spectrum shown in FIG. 5.

FIG. 4 shows signal waveform data of an X-axis component prior to excluding a low-frequency component. As shown in FIG. 4, moderate fluctuations in the axis direction of the tube were observed in the signal waveform data, and it is considered that these were caused by rocking due to the shifts of the flaw detecting probe. FIG. 5 shows a frequency spectrum extracted by applying a Fourier transform (FFT) to signal waveform data shown in FIG. 4. Here, based upon the frequency spectrum shown in FIG. 5, the frequency spectrum relating to the signal waveform data of the Y-axis component, and the like, the cut-off frequency to be used for eliminating a low-frequency component was determined to 151 Hz. FIG. 6 shows signal waveform data of the X-axis component, generated by applying an Inverse Fourier transform (IFFT) to the frequency spectrum from which the low-frequency component has been excluded by using the cut-off frequency. As shown in FIG. 6, by eliminating the low-frequency component by using the cut-off frequency of 151 Hz, the moderate fluctuations in the axis direction of the tube are eliminated so that it becomes possible to measure the noise voltage value V1 appropriately.

EXAMPLE 2

By using an eddy current testing unit having the same structure as that shown in FIG. 1, the S/N ratio defined by the above-mentioned Equation (4) was automatically measured under flaw detecting conditions shown in the following Table 1. Here, the same artificial flaws formed in the tube and the same cut-off frequency as those of Example 1 were used. Moreover, upon measuring the noise voltage value V2, the number of sampling points of respective sections into which the signal waveform data were divided was set to about 305 mm when converted into the length, and the eddy current testing was carried out over the entire length of the tube in the same manner as in Example 1.

COMPARATIVE EXAMPLE

By using the same eddy current testing unit as that shown in FIG. 1, the voltage value of an eddy current signal over the entire length of each of a tube in which the same artificial flaws were formed in the same manner as in Example 1 and a tube in which no artificial flaws were formed was obtained under the same flaw detecting conditions as shown in Table 1. Moreover, with respect to the tube with no artificial flaws formed therein, the voltage value of an eddy current signal waveform outputted from the flaw detecting unit was visually read by the operator (upon reading, a low-frequency component was also eliminated through a visual operation), and the maximum value was obtained as the noise voltage value. The S/N ratio was calculated by dividing the voltage value of an eddy current signal derived from the artificial flaws by the above-mentioned noise voltage value.

<Results of Evaluation>

Table 2 shows noise voltage values, voltage values corresponding the artificial flaws, the S/N ratio and the time required for the S/N ratio measurements, respectively measured on Examples 1 and 2 as well as on Comparative Example.

|  | Noise voltage value | Flaw signal voltage value | S/N ratio | Measuring time |
|---|---|---|---|---|
| Example 1 | 0.09 V | 4 V | 44.4 | 1 second |
| Example 2 | 0.10 V | 4 V | 40.0 | 1 second |
| Comparative Example | 0.11 V | 4 V | 36.4 | 1 minute |

As shown in Table 2, the S/N ratios automatically measured by methods relating to Examples 1 and 2 are virtually the same value as the S/N ratio measured by using a method relating to Comparative Example that is a conventional measuring method, and in contrast, the time required for the measurements on the S/N ratio is extremely shortened in the methods relating to Examples 1 and 2. These results indicate that the method relating to the present invention makes it possible to measure the S/N ratio very efficiently at least with precision as high as that of the conventional method. Here, in the above-mentioned Comparative Example, no evaluation was made with respect to a case in which the operators to read the voltage value were switched and a case in which the same operator carried out the measurements repeatedly; however, it is presumed that even when the S/N ratio is measured based upon the same eddy current waveform, the visual reading operation would cause fluctuations in the measured results depending on the skill, experience, conditions and the like of the operator. In contrast, in accordance with the methods of Examples 1 and 2, since calculation processes are carried out in accordance with the program installed in the operation unit to automatically measure the S/N ratio, the same measured results are obtained when the S/N ratio is measured based upon the same signal waveform data so that it becomes possible to obtain an S/N ratio with higher reliability in comparison with the conventional method.

The invention claimed is:

1. A method for measuring an S/N ratio in an eddy current testing on an internal surface of a pipe or tube comprising the steps of:
using a microprocessor for;
separating an eddy current signal obtained by executing an eddy current testing on the internal surface of a pipe or tube in an axis direction into an X-axis component and a Y-axis component that are different from each other by 90° in the phases thereof to obtain signal waveform data of the X-axis component and signal waveform data of the Y-axis component;
excluding predetermined low-frequency components respectively from the signal waveform data of the X-axis component and the signal waveform data of the Y-axis component thus obtained;
calculating a noise voltage value V1 defined by the following Equation (1) based upon a voltage value X(i) of the signal waveform data of the X-axis component with the low-frequency component excluded therefrom and a voltage value Y(i) of the signal waveform data of the Y-axis component with the low-frequency component excluded therefrom; and
calculating an S/N ratio defined by the following Equation (2) based upon a voltage value D of an eddy current signal corresponding to a predetermined artificial flaw, obtained by executing an eddy current testing on an internal surface of a pipe or tube with the artificial flaw formed therein, and the noise voltage value V1:

$$V1 = \pi/n \cdot \sum_{i=1}^{n}(X(i)^2 + Y(i)^2)^{1/2} \quad (1)$$

where n represents the number of samplings of the signal waveform data, $$S/N \text{ ratio} = D/V1 \quad (2).$$

2. The method for measuring an S/N ratio in an eddy current testing on an internal surface of a pipe or tube according to claim 1, wherein the step of excluding the predetermined low-frequency components comprises the steps of:
extracting a frequency spectrum by applying a Fourier transform to each of the signal waveform data of the X-axis component and the signal waveform data of the Y-axis component;
excluding the low-frequency component from the frequency spectrum thus extracted; and
applying an Inverse Fourier transform to the frequency spectrum with the low-frequency component excluded therefrom to generate signal waveform data of the X-axis component with the low-frequency component excluded therefrom and signal waveform data of the Y-axis component with the low-frequency component excluded therefrom.

3. A method for measuring an S/N ratio in an eddy current testing on an internal surface of a pipe or tube comprising the steps of:
using a microprocessor for;
separating an eddy current signal obtained by executing an eddy current testing on the internal surface of a pipe or tube in an axis direction into an X-axis component and a Y-axis component that are different from each other by 90° in the phases thereof to obtain signal waveform data of the X-axis component and signal waveform data of the Y-axis component;
excluding predetermined low-frequency components respectively from the signal waveform data of the X-axis component and the signal waveform data of the Y-axis component thus obtained;
dividing the signal waveform data of the X-axis component with the low-frequency component excluded therefrom and the signal waveform data of the Y-axis component with the low-frequency component excluded therefrom respectively into signal waveform data for each of a plurality of sections j (j=1 to N, N: an integer of 2 or more) in the axis direction of the pipe or tube;
calculating a noise voltage value V2(j) defined by the following Equation (3) for each of the divided sections j based upon a voltage value X(i, j) of the signal waveform data of the X-axis component with the low-frequency component excluded therefrom and a voltage value Y(i, j) of the signal waveform data of the Y-axis component with the low-frequency component excluded therefrom; and calculating an S/N ratio defined by the following Equation (4) based upon a voltage value D of an eddy current signal corresponding to a predetermined artificial flaw, obtained by executing an eddy current testing on an internal surface of a pipe or tube with the artificial flaw formed therein, as well as based upon a maximum value V2 over the entire sections of the noise voltage value V2(j) calculated for each of the sections j:

$$V2(j) = \pi/m \cdot \sum_{i=1}^{m} (X(i, j)^2 + Y(i, j)^2)^{1/2} \quad (3)$$

where m represents the number of samplings of the signal waveform data in each section, $$S/N \text{ ratio} = D/V2 \quad (4).$$

4. The method for measuring an S/N ratio in an eddy current testing on an internal surface of a pipe or tube according to claim 3, wherein the step of excluding the predetermined low-frequency components comprises the steps of:
   extracting a frequency spectrum by applying a Fourier transform to each of the signal waveform data of the X-axis component and the signal waveform data of the Y-axis component;
   excluding the low-frequency component from the frequency spectrum thus extracted; and
   applying an Inverse Fourier transform to the frequency spectrum with the low-frequency component excluded therefrom to generate signal waveform data of the X-axis component with the low-frequency component excluded therefrom and signal waveform data of the Y-axis component with the low-frequency component excluded therefrom.

5. A method for measuring an S/N ratio in an eddy current testing on an internal surface of a pipe or tube comprising the steps of:
   using a microprocessor for;
   separating an eddy current signal obtained by executing an eddy current testing on the internal surface of a pipe or tube in an axis direction into an X-axis component and a Y-axis component that are different from each other by 90° in the phases thereof to obtain signal waveform data of the X-axis component and signal waveform data of the Y-axis component;
   dividing the signal waveform data of the X-axis component and the signal waveform data of the Y-axis component thus obtained respectively into signal waveform data for each of a plurality of sections j (j=1 to N, N: an integer of 2 or more) in the axis direction of the pipe or tube;
   excluding predetermined low-frequency components respectively from the signal waveform data of the X-axis component and the signal waveform data of the Y-axis component for each of the divided sections j;
   calculating a noise voltage value V2(j) defined by the following Equation (3) for each of the divided sections j based upon a voltage value X(i, j) of the signal waveform data of the X-axis component with the low-frequency component excluded therefrom and a voltage value Y(i, j) of the signal waveform data of the Y-axis component with the low-frequency component excluded therefrom; and
   calculating an S/N ratio defined by the following Equation (4) based upon a voltage value D of an eddy current signal corresponding to a predetermined artificial flaw, obtained by executing an eddy current testing on an internal surface of a pipe or tube with the artificial flaw formed therein, as well as based upon a maximum value V2 over the entire sections of the noise voltage value V2(j) calculated for each of the sections j:

$$V2(j) = \pi/m \cdot \sum_{i=1}^{m} (X(i, j)^2 + Y(i, j)^2)^{1/2} \quad (3)$$

where m represents the number of samplings of the signal waveform data in each section, $$S/N \text{ ratio} = D/V2 \quad (4).$$

6. The method for measuring an S/N ratio in an eddy current testing on an internal surface of a pipe or tube according to claim 5, wherein the step of excluding the predetermined low-frequency components comprises the steps of:
   extracting a frequency spectrum by applying a Fourier transform to each of the signal waveform data of the X-axis component and the signal waveform data of the Y-axis component;
   excluding the low-frequency component from the frequency spectrum thus extracted; and
   applying an Inverse Fourier transform to the frequency spectrum with the low-frequency component excluded therefrom to generate signal waveform data of the X-axis component with the low-frequency component excluded therefrom and signal waveform data of the Y-axis component with the low-frequency component excluded therefrom.

* * * * *